US012778608B2

(12) United States Patent
Zhang et al.

(10) Patent No.: US 12,778,608 B2
(45) Date of Patent: Nov. 3, 2026

(54) INTELLIGENT THROMBUS ASPIRATION SYSTEM

(71) Applicant: Acotec Scientific Co., Ltd., Beijing (CN)

(72) Inventors: Ruijie Zhang, Beijing (CN); Jian Guo, Beijing (CN); Huiyi Gou, Beijing (CN); Cong Zhang, Beijing (CN); Tan Geng, Beijing (CN)

(73) Assignee: Acotec Scientific Co., Ltd., Beijing (CN)

( * ) Notice: Subject to any disclaimer, the term of this patent is extended or adjusted under 35 U.S.C. 154(b) by 493 days.

(21) Appl. No.: 18/542,037

(22) Filed: Dec. 15, 2023

(65) Prior Publication Data

US 2024/0206891 A1 Jun. 27, 2024

(30) Foreign Application Priority Data

Dec. 27, 2022 (CN) ........................ 202211680784.8

(51) Int. Cl.
*A61B 17/22* (2006.01)
*G16H 40/63* (2018.01)
(Continued)

(52) U.S. Cl.
CPC ............ *A61B 17/22* (2013.01); *G16H 40/63* (2018.01); *G16H 50/70* (2018.01); (Continued)

(58) Field of Classification Search
None
See application file for complete search history.

(56) References Cited

U.S. PATENT DOCUMENTS 11,730,499 B1 8/2023 Thio
2007/0060944 A1 3/2007 Boldenow
(Continued)

*Primary Examiner* — Kidest Worku
(74) *Attorney, Agent, or Firm* — Acotec Scientific IP Legal

(57) ABSTRACT

The present disclosure relates to the field of medical equipment, and provides an intelligent thrombus aspiration system, including a negative pressure suction pump, a blood collection tank, a thrombus aspiration connection unit, a suction catheter and a man-machine interaction module. The man-machine interaction module is configured to transmit a target catheter diameter of the suction catheter to the thrombus aspiration connection unit in response to a command for selecting the target catheter diameter. The thrombus aspiration connection unit is configured to obtain historical treatment data corresponding to the target catheter diameter, cluster the historical treatment data through a neural network model so as to obtain a target suction frequency, a target suction duration and a target suction negative pressure corresponding to the target catheter diameter, and control the negative pressure suction pump and the suction catheter in accordance with the target suction frequency, the target suction duration and the target suction negative pressure. According to the present disclosure, it is able to automatically generate an optimum suction strategy corresponding to the target catheter diameter, determine a suction state of the suction catheter, thereby to reduce the amount of bleeding of a patient without reducing the suction efficiency, and remarkably improve a clinical effect of thrombus aspiration.

9 Claims, 6 Drawing Sheets

(51) Int. Cl.
*G16H 50/70* (2018.01)
*A61B 17/00* (2006.01)

(52) U.S. Cl.
CPC ............... *A61B 2017/00022* (2013.01); *A61B 2017/22079* (2013.01); *A61B 2217/005* (2013.01)

(56) References Cited

U.S. PATENT DOCUMENTS

2011/0230859 A1 9/2011 Galdonik
2012/0016344 A1 1/2012 Kusakabe
2012/0041475 A1* 2/2012 Ferrera ................ A61B 17/221 606/200
2012/0253313 A1 10/2012 Galdonik
2012/0272955 A1* 11/2012 Cool .................. A61M 16/024 128/207.14
2015/0257774 A1 9/2015 Galdonik
2016/0166265 A1 6/2016 Nita
2016/0166266 A1 6/2016 Nita
2017/0238951 A1 8/2017 Yang
2017/0239440 A1 8/2017 Yang
2017/0252536 A1 9/2017 Yang
2018/0093068 A1 4/2018 Nagao
2018/0242989 A1 8/2018 Nita
2018/0263642 A1 9/2018 Nita
2018/0303498 A1 10/2018 Galdonik
2018/0353194 A1 12/2018 Shaffer
2019/0142452 A1 5/2019 Trosper
2019/0336727 A1 11/2019 Yang
2020/0001046 A1 1/2020 Yang
2020/0155181 A1 5/2020 Yang
2020/0170666 A1 6/2020 Trosper
2020/0297363 A1* 9/2020 Look ..................... A61M 1/743
2020/0297972 A1 9/2020 Yee
2020/0345987 A1* 11/2020 Jalgaonkar .......... A61M 25/005
2020/0367917 A1 11/2020 Teigen
2020/0383698 A1 12/2020 Miao
2020/0397957 A1 12/2020 Teigen
2021/0128182 A1 5/2021 Teigen
2021/0315598 A1 10/2021 Buck
2021/0353323 A1 11/2021 Teigen
2021/0361314 A1* 11/2021 Teigen ................... A61B 17/22
2021/0378696 A1 12/2021 Yang
2022/0211975 A1 7/2022 Yang
2022/0280171 A1 9/2022 Teigen
2023/0026412 A1 1/2023 Teigen
2023/0116973 A1 4/2023 Yang
2024/0000469 A1 1/2024 Teigen

* cited by examiner

INTELLIGENT THROMBUS ASPIRATION SYSTEM

TECHNICAL FIELD

The present disclosure relates to the field of medical rehabilitation, in particular to an intelligent thrombus aspiration system.

BACKGROUND

Along with the growth in the living standard, the incidence of thrombotic diseases increases, and due to the thrombotic disease, the flow of blood in a patient is blocked or completely interrupted. The embolization in a blood vessel is seriously risky, e.g., crippling or even death. Usually, in the related art, a suction catheter is used to eliminate foreign matters, e.g., thrombus, in the blood vessel. To be specific, the suction catheter is transferred to a position where the thrombus occurs, and a negative pressure is applied to a proximal end of the suction catheter so that the foreign matter moves along an internal cavity of the suction catheter to the outside, so as to re-establish the blood circulation.

It is found that, an existing thrombus aspiration system is short of intelligence, i.e., it is impossible to generate an optimum suction scheme in accordance with a condition of the patient and a catheter diameter of the suction catheter. Usually, a suction strategy is provided by a doctor based on his own experience, so the effectiveness and effect of the operation are adversely affected to some extent.

In addition, the existing thrombus aspiration system performs a suction operation continuously, and it is impossible to adjust a suction frequency in accordance with a current suction state. For a thrombus with a large adhesion, e.g., a chronic thrombus or a large thrombus, a suction duration is too long, leading to a large amount of bleeding as well as additional pain, even complications. Hence, a clinical effect of the existing thrombus aspiration system is poor.

SUMMARY

An object of the present disclosure is to provide an intelligent thrombus aspiration system, so as to at least partially solve the above-mentioned problems.

The present disclosure provides in some embodiments an intelligent thrombus aspiration system, including a negative pressure suction pump, a blood collection tank, a thrombus aspiration connection unit, a suction catheter and a man-machine interaction module. The thrombus aspiration connection unit is coupled to the negative pressure suction pump and the suction catheter through an air channel, and the blood collection tank is detachably coupled to the thrombus aspiration connection unit. The man-machine interaction module is configured to transmit a target catheter diameter of the suction catheter to the thrombus aspiration connection unit in response to a command for selecting the target catheter diameter. The thrombus aspiration connection unit is configured to: obtain a plurality of groups of historical treatment data corresponding to the target catheter diameter, each group of historical treatment data at least including diagnosis information and suction data; input the diagnosis information and the plurality of groups of historical treatment data into a neural network, so that a word-to-vector model of the neural network concatenates and vectorizes the diagnosis information in each group of historical treatment data and outputs a plurality of concatenated vectors to a vector fusion model, the vector fusion model being configured to identify the diagnosis information belonging to a same class in each group of historical treatment data; cluster the historical treatment data corresponding to the suction data having a same class as the diagnosis information and having a deviation value smaller than a predetermined threshold, so as to obtain a plurality of historical treatment data classes; calculate the quantity of groups of historical treatment data in each historical treatment data class to generate a quantity label, identify class diagnosis information corresponding to each historical treatment data class, and select a matched historical treatment data class in accordance with the target diagnosis information, the quantity label and the class diagnosis information; and take an average value of the suction data in the selected historical treatment data class as target suction data corresponding to the target catheter diameter of the suction catheter.

In a possible embodiment of the present disclosure, the diagnosis information includes physiological information, drug information and disease information about a patient.

In a possible embodiment of the present disclosure, the suction data includes a suction frequency, a suction duration and a suction negative pressure.

In a possible embodiment of the present disclosure, the thrombus aspiration connection unit further includes a pressure sensor in the air channel, and the thrombus aspiration connection unit is further configured to determine a current suction state in accordance with a negative pressure value detected by the pressure sensor after the air channel is closed, and adjust a current suction frequency in accordance with the current suction state.

In a possible embodiment of the present disclosure, the suction state includes a blood-drawing state, a thrombus-drawing state and a fully-blocking state.

In a possible embodiment of the present disclosure, the thrombus aspiration connection unit further includes a control circuit board and an electromagnetic valve, the control circuit board is configured to open or close the air channel through controlling the electromagnetic valve to be turned on or off, and the suction frequency depends on a switching frequency of the electromagnetic valve.

In a possible embodiment of the present disclosure, the thrombus aspiration connection unit further includes a state indicator and a loudspeaker, and when the current suction state has been determined in accordance with the negative pressure value detected by the pressure sensor, the control circuit board is further configured to control the state indicator to be in an on state and control the loudspeaker to beep.

In a possible embodiment of the present disclosure, the thrombus aspiration connection unit further includes a double-row pipe, the double-row pipe includes an air-channel pipe and a power line pipe, one end of the air-channel pipe is coupled to an internal air channel of the thrombus aspiration connection unit, another end of the air-channel pipe is coupled to the suction catheter through a single-lumen pipe and a Luer taper, one end of the power line pipe is coupled to a switch, and another end of the power line pipe is coupled to the control circuit board.

In a possible embodiment of the present disclosure, the thrombus aspiration connection unit further includes the internal air channel and a three-way valve, a first end of the three-way valve is in communication with the internal air channel, a second end of the three-way valve is in communication with the air-channel pipe, and a third end of the three-way valve is coupled to the pressure sensor.

In a possible embodiment of the present disclosure, the thrombus aspiration connection unit further includes a sealing joint, one or more protruding sealing rings is arranged in an internal chamber of the sealing joint, one end of the sealing joint is coupled to the internal air channel, another end of the sealing joint is fixed onto a housing of the thrombus aspiration connection unit, the sealing joint is inserted into an opening in a boss of the blood collection tank so that each sealing ring is in hermetical engagement with the boss of the blood collection tank, and an anti-vibration gasket is arranged between the blood collection tank and the housing.

According to the intelligent thrombus aspiration system in the embodiments of the present disclosure, it is able to automatically provide an optimum suction strategy in accordance with the target catheter diameter of the suction catheter selected by a doctor, the diagnosis information about the patient, and the historical treatment data. In addition, through discontinuous suction, it is able to automatically determine the suction state of the suction catheter, and control the suction operation in different suction states, thereby to remarkably reduce the amount of bleeding of the patient without reducing the suction efficiency.

BRIEF DESCRIPTION OF THE DRAWINGS

The other features, purposes and advantages of the present disclosure will become more apparent through reading the description about the nonrestrictive embodiments with reference to the following drawings.

DETAILED DESCRIPTION

Figure 1:
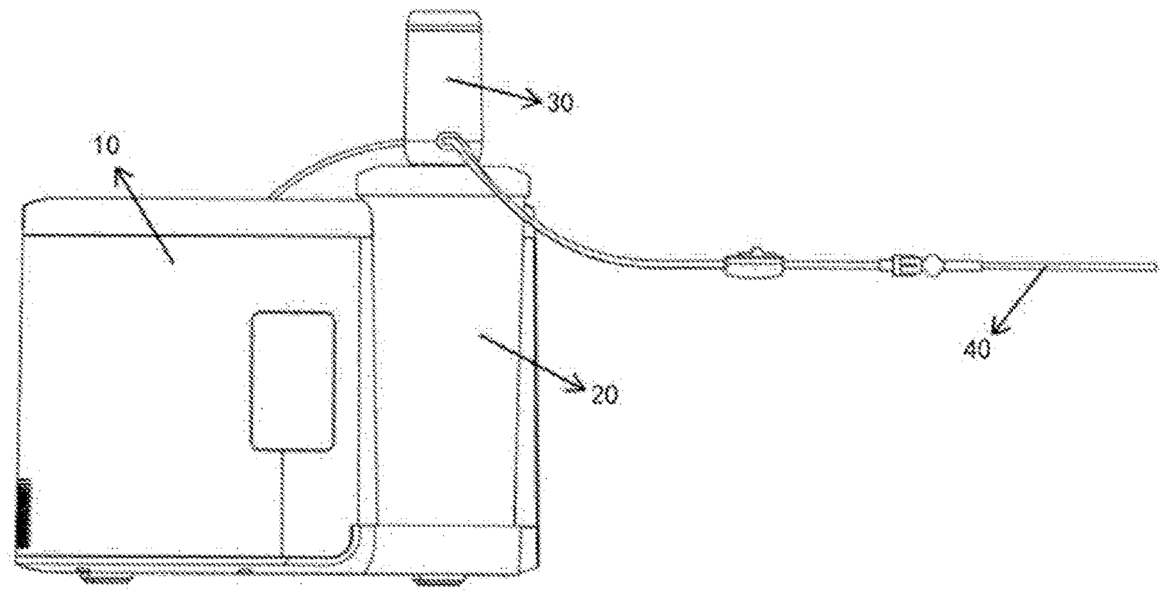
FIG. 1 is a front view of an intelligent thrombus aspiration system according to one embodiment of the present disclosure.

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

The terms involved in the embodiments of the present disclosure are merely used to describe specific embodiments rather than to define the scope of the present disclosure.

Unless otherwise defined, any singular form ("a", "an" and "the") involved in the specification and the appended claims is not intended to exclude a plurality of features or components.

It should be appreciated that, such words as "first", "second" and "third" are merely used to differentiate different components rather than to represent any order, number or importance.

Depending on the context, the word "if" may be understood as "when" or "in response to the determination or detection of". Similarly, depending on the context, the expression "if it is determined that" may be understood as "when it is determined" or "in response to the determination of", and the expression "if it is detected that" may be understood as "when it is detected that" or "in response to the detection of".

It should be further appreciated that, such words as "on", "under", "left" and "right" may indicate directions or positions as viewed in the drawings, and shall not be construed as limiting the present disclosure. In addition, when one element is formed on or under another element, the element is directly formed on or under the other element, or an intermediate element may be arranged therebetween.

Figure 2:
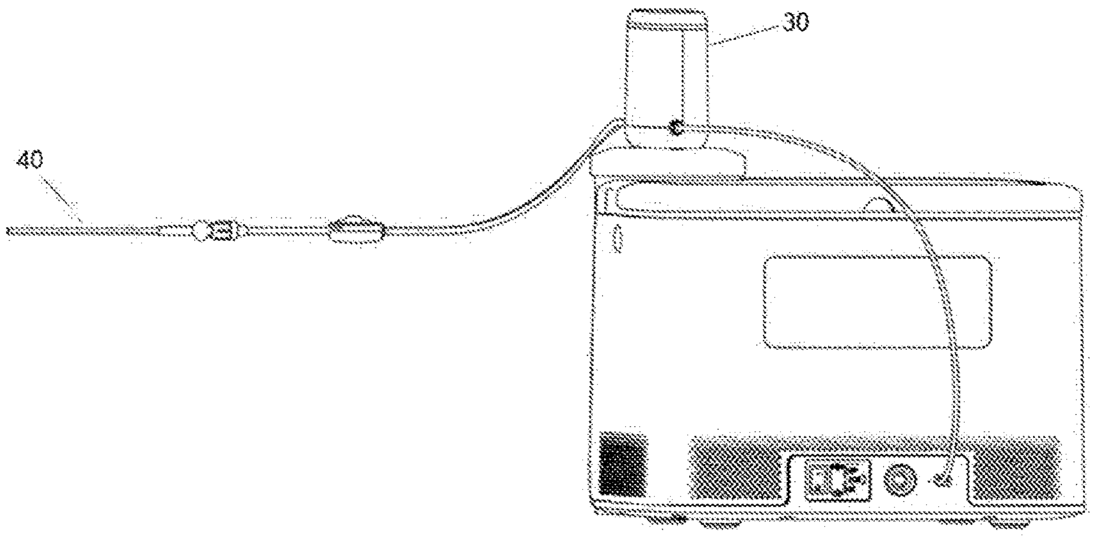
FIG. 2 is a back view of the intelligent thrombus aspiration system according to one embodiment of the present disclosure.

As shown in FIGS. 1 and 2, the present disclosure provides in some embodiments an intelligent thrombus aspiration suction system, which includes a negative pressure suction pump 10, a blood collection tank 20, a thrombus aspiration connection unit 30, a suction catheter 40 and a man-machine interaction module (not shown).

The man-machine interaction module is configured to transmit a target catheter diameter of the suction catheter 40 to the thrombus aspiration connection unit 30 in response to a command for selecting the target catheter diameter. The thrombus aspiration connection unit 30 is configured to obtain N groups of historical treatment data corresponding to the target catheter diameter, and cluster the N groups of historical treatment data through a neural network model to obtain a target suction frequency, a target suction duration and a target suction negative pressure. Each group of historical treatment data at least includes diagnosis information, a suction frequency, a suction duration and a suction negative pressure, and N is an integer greater than or equal to 2. The thrombus aspiration connection unit 30 is coupled to the negative pressure suction pump 10 and an air channel of the suction catheter 40, and further configured to control the negative pressure suction pump 10 and the suction catheter 40 in accordance with the target suction frequency, the target suction duration and the target suction negative pressure, so as to suction a thrombus of a patient. The negative pressure suction pump 10 is configured to provide a negative pressure source. The blood collection tank 20 is coupled to the thrombus aspiration connection unit 30, and configured to collect the thrombus.

To be specific, the target catheter diameter is determined in accordance with a diameter of a blood vessel of the patient where a lesion occurs, and different blood vessels have different diameters. The suction catheter is selected by a doctor in accordance with a lesion position, so as to ensure that an outer diameter of the suction catheter is smaller than an inner diameter of the blood vessel. For example, when a blood vessel where the thrombus occurs has a large diameter (e.g., femoral artery/vein, or pulmonary vein), the suction catheter with a large catheter diameter is selected, so as to increase the suction efficiency and a suction force. When a blood vessel where the thrombus occurs has a small diameter (e.g., infrapopliteal artery/vein, cerebral artery/vein, or carotid artery/vein), the suction catheter with a small catheter diameter is selected, so as to facilitate the intervention of the suction catheter to the position where the lesion occurs.

In a possible embodiment of the present disclosure, the man-machine interaction module is a computing device with a touch screen, and the doctor is capable of selecting the suction catheter with the target catheter diameter suitable for the lesion position in the man-machine interaction module.

It should be appreciated that, when a laminar motion occurs for a fluid in a horizontal, circular tube, there is the following relationship between a volume flow rate Q and a suction negative pressure $\Delta p$ at two ends of the tube, a radius r of the tube, a length L of the tube and a coefficient $\eta$ of viscosity of the fluid: $Q=\pi*r^4*\Delta p/(8\ \eta L)$. In other words, the suction amount of the thrombus or blood is controlled through adjusting the suction negative pressure. In addition, the suction is performed discontinuously, and it is further necessary to determine the suction frequency and the suction duration. Hence, after the selection of the target catheter diameter, the suction frequency, the suction duration and the suction negative pressure need to be determined.

In the embodiments of the present disclosure, the historical treatment data corresponding to the target catheter diameter is clustered through the neural network model, and then the suction frequency, the suction duration and the suction negative pressure best matching the target catheter diameter are calculated. During the discontinuous suction, the target suction frequency, the target suction duration and the target suction negative pressure are calculated through an artificial intelligence algorithm in accordance with the historical treatment data, so as to generate a suction strategy for the suction catheter with the target catheter diameter.

To be specific, N groups of historical treatment data corresponding to the target catheter diameter are obtained, the diagnosis information, the suction frequency, the suction duration and the suction negative pressure in each group of historical treatment data are compared with those in the other groups of historical treatment data through the neural network model, and then a class of a relation between each group of historical treatment data and the other groups of historical treatment data (an equivalent relation or a contradictory relation) is outputted. The diagnosis information mainly includes physiological information, drug information and disease information about the patient. Next, the N groups of historical treatment data are clustered in accordance with the class of the relation, and the groups of historical treatment data having the equivalence relation are gather to form a historical treatment data class, so as to obtain a plurality of historical treatment data classes. Each historical treatment data class includes a plurality of groups of historical treatment data. Then, the quantity of groups of historical treatment data in each historical treatment data class and the corresponding diagnosis information are calculated. The larger the quantity of groups of historical treatment data, the more the cases where the suction is performed with the suction frequency, the suction duration and the suction negative pressure in the historical treatment data class. To be specific, candidate historical treatment data classes where the diagnosis information is the same as or similar to target diagnosis information about the patient are selected, a target historical treatment data class with the maximum quantity of groups of historical treatment data is determined in the candidate historical treatment data classes, and then the suction frequency, the suction duration and the suction negative pressure in the target historical treatment data class are used as the target suction frequency, the target suction duration and the target suction negative pressure respectively.

The negative pressure suction pump 10 provides the negative pressure source for the entire intelligent thrombus aspiration suction system. The blood collection tank 20 collects the blood and thrombus. The thrombus aspiration connection unit 30 is coupled to the negative pressure suction pump 10 and the air channel of the suction catheter 40. In response to the target catheter diameter of the suction catheter determined by the man-machine interaction module, the thrombus aspiration connection unit 30 automatically determines the suction strategy, e.g., the target suction frequency, the target suction duration and the target suction negative pressure, and controls the air channel in accordance with the suction strategy, so as to achieve the discontinuous suction.

According to the intelligent thrombus aspiration system in the embodiments of the present disclosure, the suction catheter is selected in accordance with the lesion position, and the suction frequency, the suction duration and the suction negative pressure matching the condition of the patient and the catheter diameter of the suction catheter are determined in accordance with the historical treatment data, so as to achieve the discontinuous suction. On one hand, through selecting the catheter diameter of the suction catheter, it is able to ensure that the outer diameter of the suction catheter is smaller than the inner diameter of the blood vessel, thereby to facilitate the intervention of the suction catheter to the lesion position. On the other hand, through the discontinuous suction, it is able to remarkably reduce the amount of bleeding of the patient without reducing the suction efficiency. In addition, based on the suction strategy obtained through the artificial intelligence algorithm, it is able to remarkably improve a suction effect of the thrombus.

Figure 3:
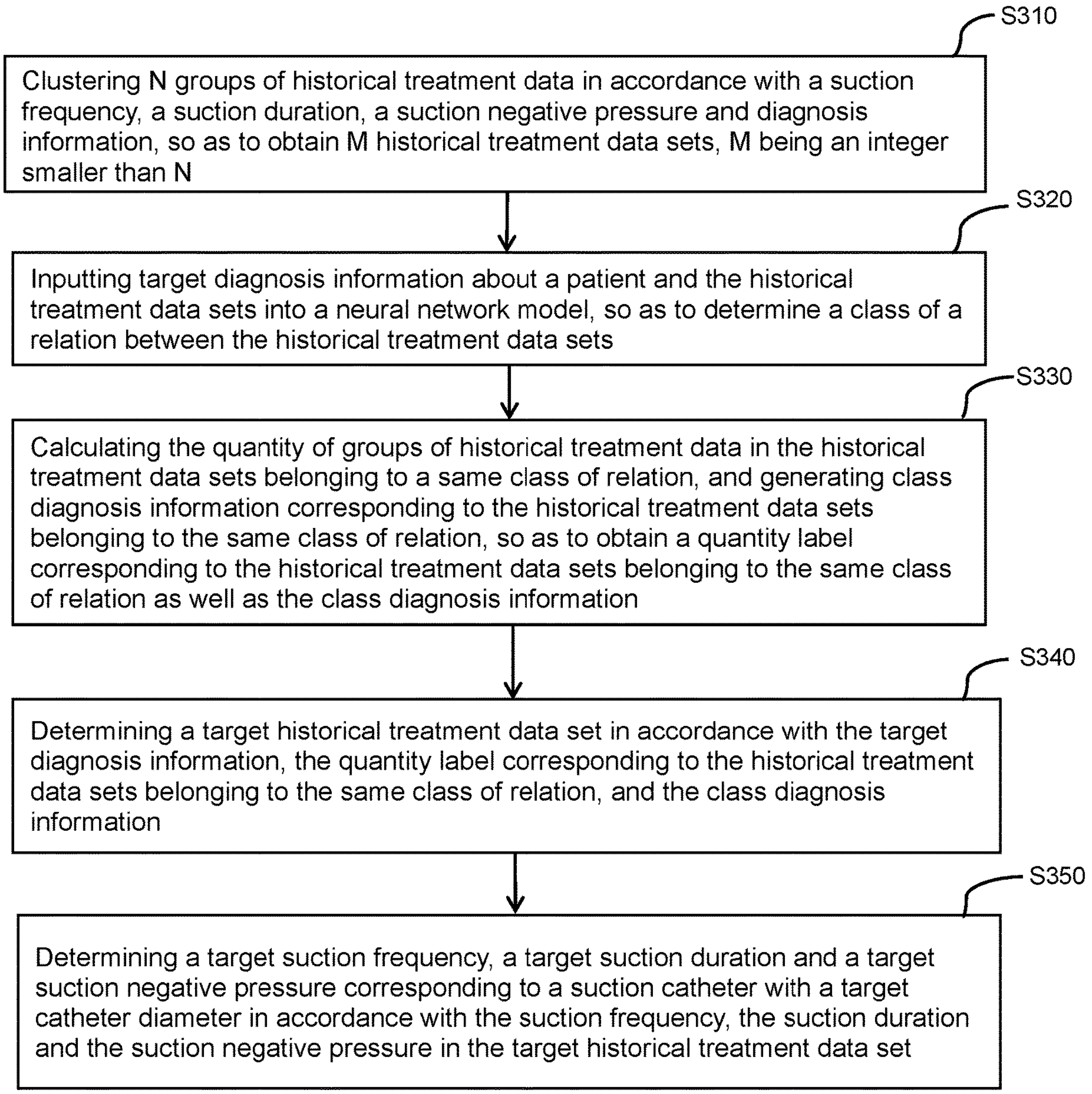
FIG. 3 is a flow chart of a method for generating a suction strategy for a suction catheter with a target catheter diameter according to one embodiment of the present disclosure.

As shown in FIG. 3, the process of clustering the N groups of historical treatment data through the neural network model so as to obtain the target suction frequency, the target suction duration and the target suction negative pressure corresponding to the target catheter diameter includes the following steps.

Step S310: clustering the N groups of historical treatment data in accordance with the suction frequency, the suction duration, the suction negative pressure and the diagnosis information, so as to obtain M historical treatment data sets, where M is an integer smaller than N.

To be specific, the groups of historical treatment data having same or similar diagnosis information, suction frequencies, suction durations and suction negative pressures are clustered to obtain M historical treatment data sets. It should be appreciated that, the diagnosis information may be calculated through a context similarity calculation method, and the suction frequencies, the suction durations and the suction negative pressures may be fuzzy consistent, i.e., they may be considered as consistent when a deviation value is smaller than a predetermined threshold. The predetermined threshold is set according to the experience.

Step S320: inputting the target diagnosis information about the patient and the historical treatment data sets into the neural network model, so as to determine a class of a relation between the historical treatment data sets.

To be specific, the class of the relation includes an equivalence relation in which two historical treatment data sets are capable of being clustered again or a contradictory relation in which two historical treatment data sets are incapable of being clustered again. The target diagnosis information plays an important role in determining the class of the relation between the historical treatment data sets. For example, the suction frequency, the suction duration and the suction negative pressure in a historical treatment data set A are the same as or similar to those in a historical treatment data B, but the diagnosis information is different. When the target diagnosis information about a target patient includes that statins are taken by the target patient, the diagnosis information "simvastatin" in the historical treatment data set A and "rosuvastatin" in the historical treatment data set B are both statins, so the class of the relation between the historical treatment data sets A and B is an equivalence relation. When the target diagnosis information about the target patient includes that simvastatin is taken by the target patient, the diagnosis information "simvastatin" in the historical treatment data set A is different from "rosuvastatin" in the historical treatment data set B. Every two of the M historical treatment data sets obtained in Step S310 are combined, and inputted into the neural network model together with the target diagnosis information, so as to determine the class of the relation between any two historical treatment data sets.

Step S330: calculating the quantity of groups of historical treatment data in the historical treatment data sets belonging to a same class of relation, and generating the class diagnosis information corresponding to the historical treatment data sets belonging to the same class of relation, so as to obtain a quantity label corresponding to the historical treatment data sets belonging to the same class of relation as well as the class diagnosis information.

To be specific, the quantity of groups of historical treatment data in the historical treatment data sets belonging to a same class of relation is counted. In the above step, the suction frequencies, the suction durations and the suction negative pressures in the historical treatment data sets belonging to the same class of relation are the same or similar, so the quantity of groups may be used to determine a degree of confidence when the treatment is performed with the suction frequency, the suction duration and the suction negative pressure. Further, word segmentation is performed on the diagnosis information in each group of historical treatment data, and the class diagnosis information is generated in accordance with an occurrence frequency of a word. For example, the word segmentation is performed on "辛伐他汀(simvastatin)" so as to obtain "辛(sim)", "伐(va)" and "他汀(statin)", and the word segmentation is performed on "瑞舒伐他汀 (rosuvastatin)" so as to obtain "瑞(ro)", "舒(su)", "伐(va)" and"他汀(statin)", so the class diagnosis information includes "他汀(statin)".

Step S340: determining a target historical treatment data set in accordance with the target diagnosis information, the quantity label corresponding to the historical treatment data sets belonging to a same class of relation, and the class diagnosis information.

To be specific, the class diagnosis information identical or similar to the target diagnosis information about the patient is selected. When there is merely one historical treatment data set corresponding to the class diagnosis information, the historical treatment data set is selected as the target historical treatment data set. When there are two or more historical treatment data sets corresponding to the class diagnosis information, a historical treatment data set with a maximum quantity of groups of historical treatment data is selected as the target historical treatment data set.

Step S350: determining the target suction frequency, the target suction duration and the target suction negative pressure corresponding to the suction catheter with the target catheter diameter in accordance with the suction frequency, the suction duration and the suction negative pressure in the target historical treatment data set.

In a possible embodiment of the present disclosure, average values of the suction frequencies, the suction durations and the suction negative pressures in each group of target historical treatment data are calculated as the target suction frequency, the target suction duration and the target suction negative pressure corresponding to the suction catheter with the target catheter diameter respectively. In addition, maximum values or minimum values of the suction frequencies, the suction durations and the suction negative pressures in each group of target historical treatment data are calculated as the target suction frequency, the target suction duration and the target suction negative pressure corresponding to the suction catheter with the target catheter diameter respectively, which is related to the doctor's experience and will not be particularly defined herein.

In a possible embodiment of the present disclosure, the diagnosis information in the historical treatment data may be further classified as follows.

Step S410: inputting the target diagnosis information and each historical treatment data set into the neural network model, and concatenating and vectorizing the target diagnosis information and each historical treatment data set, so as to output M concatenated vectors.

Step S420: inputting the M concatenated vectors into a vector fusion model, so as to obtain a class of relation between the historical treatment data sets.

In the embodiments of the present disclosure, the target diagnosis information and the diagnosis information in each historical treatment data set are vectorized through a neural network model, e.g., a word-to-vector (word2vec) model. Next, the vectorized target diagnosis information is concatenated with the vectorized diagnosis information in each historical treatment data set so as to obtain the M concatenated vectors. Then, the concatenated vectors are calculated through the vector fusion model so as to obtain the class diagnosis information in each group of historical treatment data.

Figure 4:
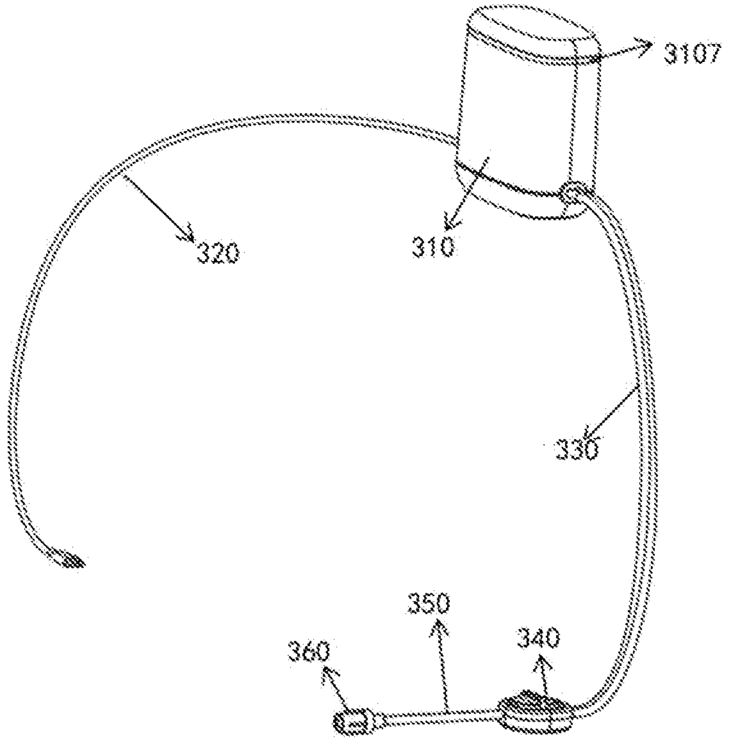
FIG. 4 is a schematic view showing a thrombus aspiration connection unit according to one embodiment of the present disclosure.

In a possible embodiment of the present disclosure, as shown in FIG. 4, the thrombus aspiration connection unit 30 includes a controller 310, a cable 320, a double-row pipe 330, a switch 340, a single-lumen pipe 350 and a Luer taper 360.

The controller 310 is of a cuboid shape, and two ends of the controller 310 are coupled to the cable 320 and the double-row pipe 330. As a core of the thrombus aspiration connection unit 30, the controller 310 is configured to generate, through an artificial intelligence algorithm, the target suction frequency, the target suction duration and the target suction negative pressure, and control the negative pressure suction pump 10 and an electromagnetic valve 3101.

One end of the cable 320 is provided with a Universal Serial Bus (USB) interface coupled to the negative pressure suction pump 10. In a possible embodiment of the present disclosure, the cable 320 is a multi-core cable with a shielding layer and a protection layer. Power is supplied to the controller 310 through the cable 320. In addition, the cable 320 includes a grounded line, and a signal transmission line through which an operating state of the negative pressure suction pump 10 is transmitted to the controller 310 and an operating state of the controller 310 is transmitted to the negative pressure suction pump 10.

Figure 5:
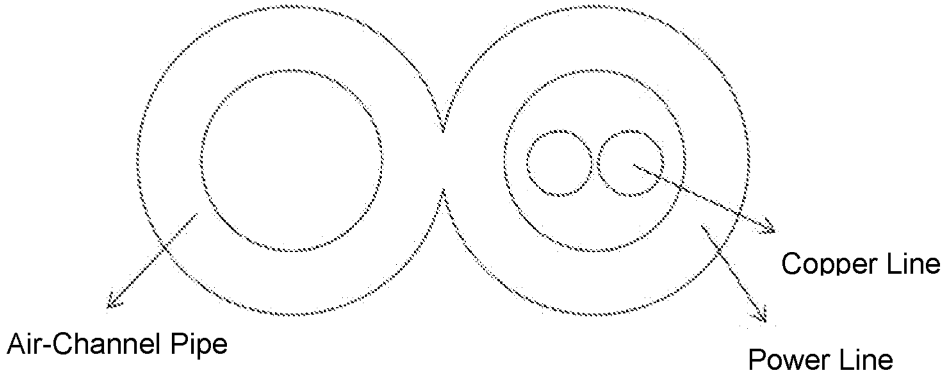
FIG. 5 is a sectional view of a double-row pipe according to one embodiment of the present disclosure.

As shown in FIG. 5, the double-row pipe 330 includes an air-channel pipe and a power line pipe. One end of the air-channel pipe is coupled to a three-way valve in the controller 310, and another end of the air-channel pipe is in communication with, or formed integrally with, the single-lumen pipe 350. Two copper lines are provided in the power line pipe, and one end of each copper line is coupled to the switch 340, and another end thereof is coupled to a control circuit board 3102 of the controller 310 for the signal transmission.

In a possible embodiment of the present disclosure, for ease of identification, a color of the power line pipe is different from a color of the air-channel pipe.

In a possible embodiment of the present disclosure, the air-channel pipe is made of a transparent polymer material, e.g., polyvinyl chloride (PVC), polyurethane (PU), or silica gel, so as to facilitate the check of the suction state.

The switch 340 is capable of switched between an ON state in which the electromagnetic valve 3101 is controlled by the control circuit board 3102 of the controller 10 in accordance with the suction state and an OFF state in which the electromagnetic valve is in an always-off state.

One end of the single-lumen pipe 350 is coupled to the Luer taper 360, and another end thereof is coupled to, or formed integrally with, the air-channel pipe. In a possible embodiment of the present disclosure, the single-lumen pipe 350 is made of a polymer material.

In a possible embodiment of the present disclosure, the Luer taper 360 is rapidly engaged with a seat of the suction catheter 40, so as to enable the thrombus aspiration connection unit to be in hermetical communication with the suction catheter.

Figure 6:
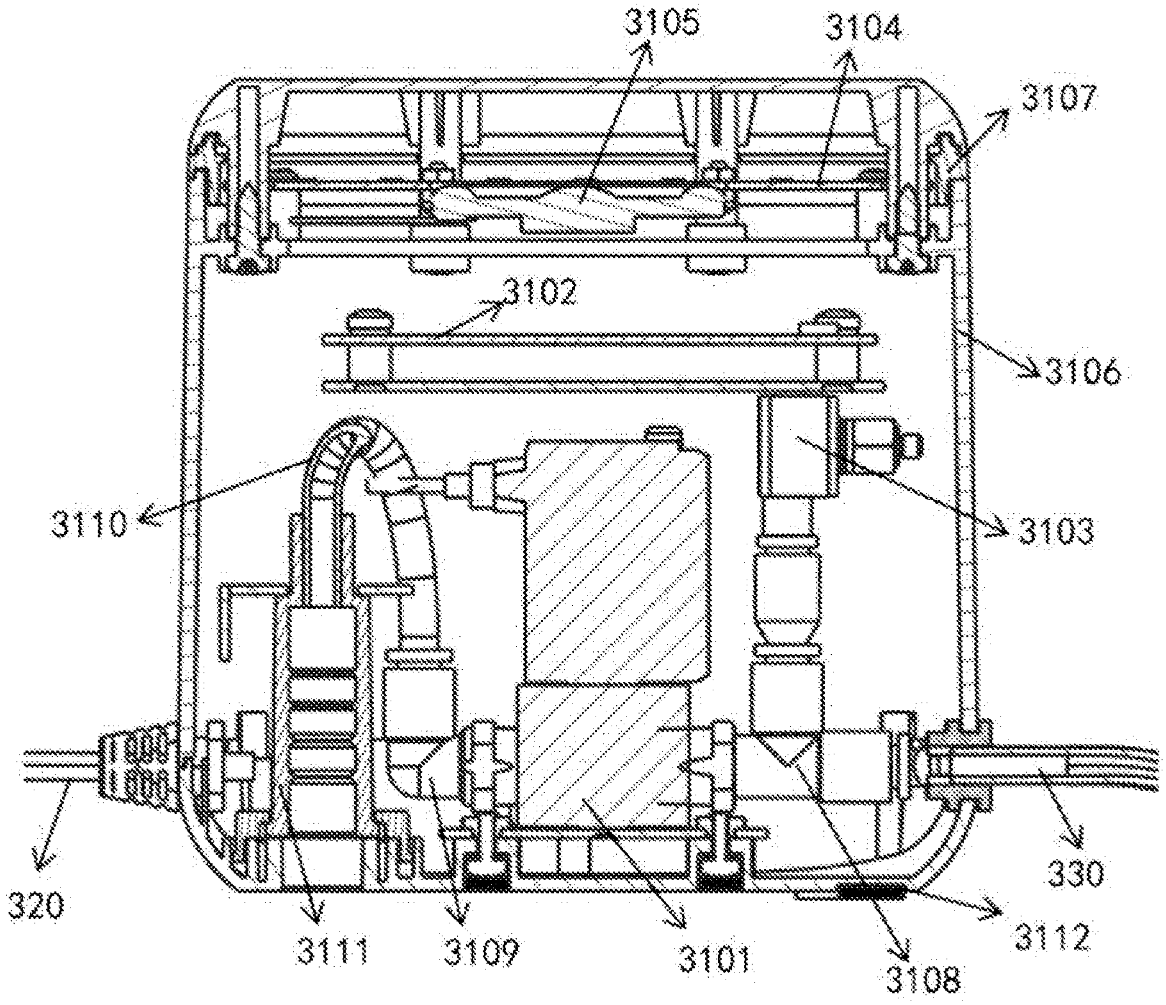
FIG. 6 is a schematic view showing an internal structure of the thrombus aspiration connection unit according to one embodiment of the present disclosure.

In a possible embodiment of the present disclosure, as shown in FIG. 6, the controller 310 includes the electromagnetic valve 3101, the control circuit board 3102, a pressure sensor 3103, a light board or state indicator 3104, a loudspeaker 3105, a housing 3106, a transparent cover 3107, a T-like joint 3108, an adapter 3109, a braided hose 3110, a sealing joint 3111 and an anti-vibration gasket 3112.

The negative pressure suction pump 10 is controlled by the electromagnetic valve 3101, and a switching frequency of the electromagnetic valve is controlled by the control circuit board 3102. In a possible embodiment of the present disclosure, the electromagnetic valve 3101 is an always-on or always-off electromagnetic valve. When the electromagnetic valve 3101 is turned on, the suction operation is performed through the suction catheter 40. When the electromagnetic valve 3101 is turned off, the suction operation is stopped. The electromagnetic valve 3101 is fixed onto the housing 3106 through a screw.

The control circuit board 3102 is configured to generate the target suction frequency, the target suction duration and the target suction negative pressure through the artificial intelligence algorithm, so as to control the electromagnetic valve 3101. In a possible embodiment of the present disclosure, the control circuit board 3102 is further configured to control the loudspeaker 3105 to generate different sounds, and control the light board 3104 to emit light in different colors. To be specific, the suction states of the suction catheter are indicated through different sounds and light in different colors.

The pressure sensor 3103 is configured to detect a negative pressure value in an air channel of the negative pressure suction pump 10, covert the negative pressure value into an electric signal, and transmit the electric signal to the control circuit board 3102. The control circuit board 3102 determines the suction state of the suction catheter 40 in accordance with a change in the negative pressure value.

The light board 3104 is a hollow, rectangular circuit board, and a plurality of light-emitting diodes is arranged at a periphery of the circuit board. Light emitted by the light-emitting diodes passes through the transparent cover. The loudspeaker 3105 is surrounded by the light board 3104.

The housing 3106 is fixed to the transparent cover 3107 through a screw, and the housing 3106 is provided with a plurality of holes surrounding the loudspeaker 3105. In a possible embodiment of the present disclosure, the housing 3106 and the transparent cover 3107 are made of plastics, and the housing is non-transparent.

The T-like joint 3108 is coupled to the pressure sensor 3103, the electromagnetic valve 3101 and the air channel. One end of the adapter 3109 is coupled to the electromagnetic valve 3101, and another end thereof is coupled to the braided hose 3110. The braided hose 3110 is provided with a braided layer made of metal or nylon, so as to prevent the braided hose from being deformed. The braided hose 3110 is a single-lumen pipe made of a polymer material, so as to prevent an inner diameter of the braided hose 3110 from changing when it is bent.

One or more protruding sealing rings is provided in an internal chamber of the sealing joint 3111. One end of the sealing joint is coupled to the braided hose 3110, and another end thereof is fixed onto the housing 3106. The sealing joint 3111 is inserted into a boss of the blood collection tank 20 so that each sealing ring is in hermetical engagement with the boss of the blood collection tank 20, and thereby the air channel of the negative pressure suction pump 10 is in communication with the controller 310. In a possible embodiment of the present disclosure, the sealing joint 3111 is of a hollow structure made of PVC, PU or silica gel.

The anti-vibration gasket 3112 is fixed onto a bottom of the controller 310, and the controller 310 is inserted into the boss of the blood collection tank 10. The anti-vibration gasket 3112 is arranged between the blood collection tank 10 and the housing 3106, so as to reduce the vibration from the negative pressure suction pump 10. In a possible embodiment of the present disclosure, the anti-vibration gasket 3112 is made of PVC, PU or silica gel.

Figure 7:
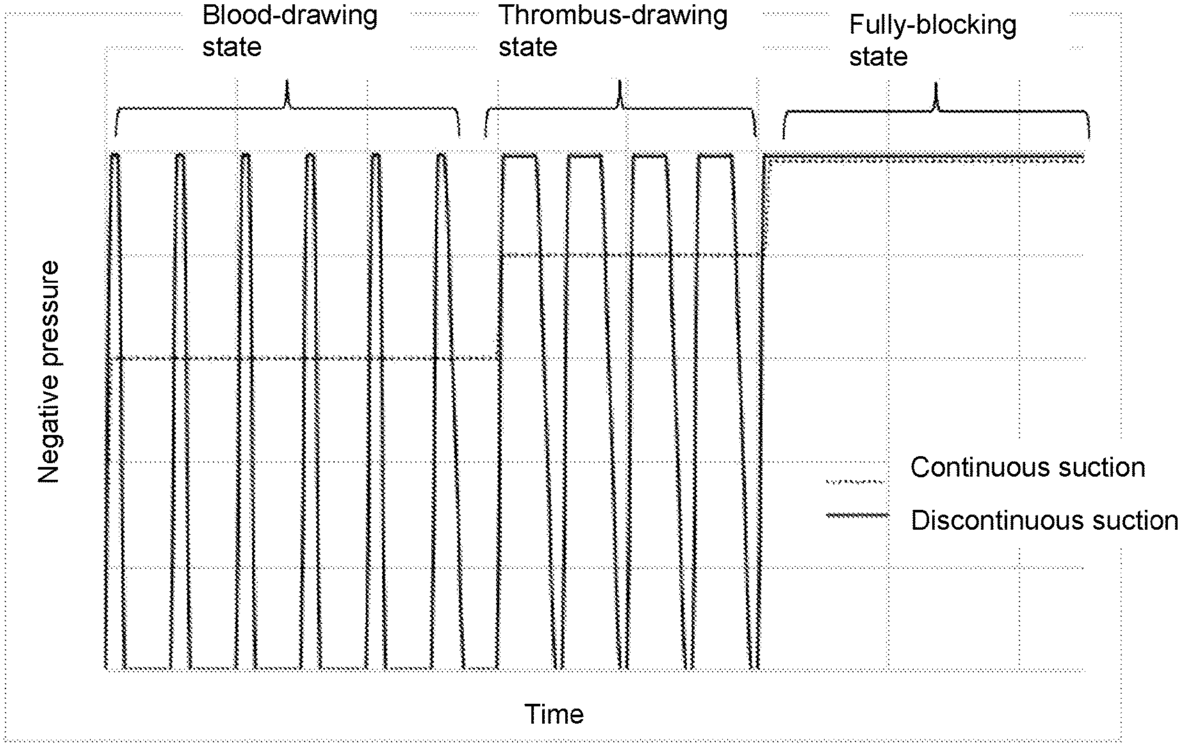
FIG. 7 is a diagram showing suction frequencies corresponding to different suction states according to one embodiment of the present disclosure.

In a possible embodiment of the present disclosure, as shown in FIG. 7, the intelligent thrombus aspiration system is provided with various suction states, i.e., a blood-drawing state, a thrombus-drawing state and a fully-blocking state corresponding to different suction frequencies and different suction forces. The controller 310 controls the electromagnetic valve 3101 in different suction states. For example, a small suction force is provided in the blood-drawing state, a large suction force is provided in the thrombus-drawing state, and a maximum suction force is provided in the fully-blocking state. In this way, it is able to remarkably reduce the amount of bleeding of the patient without reducing the suction efficiency. In addition, through the discontinuous suction, it is able to increase the suction force at a distal end of the suction catheter 40, thereby to facilitate the suction of the large or chronic thrombus.

Figure 8:
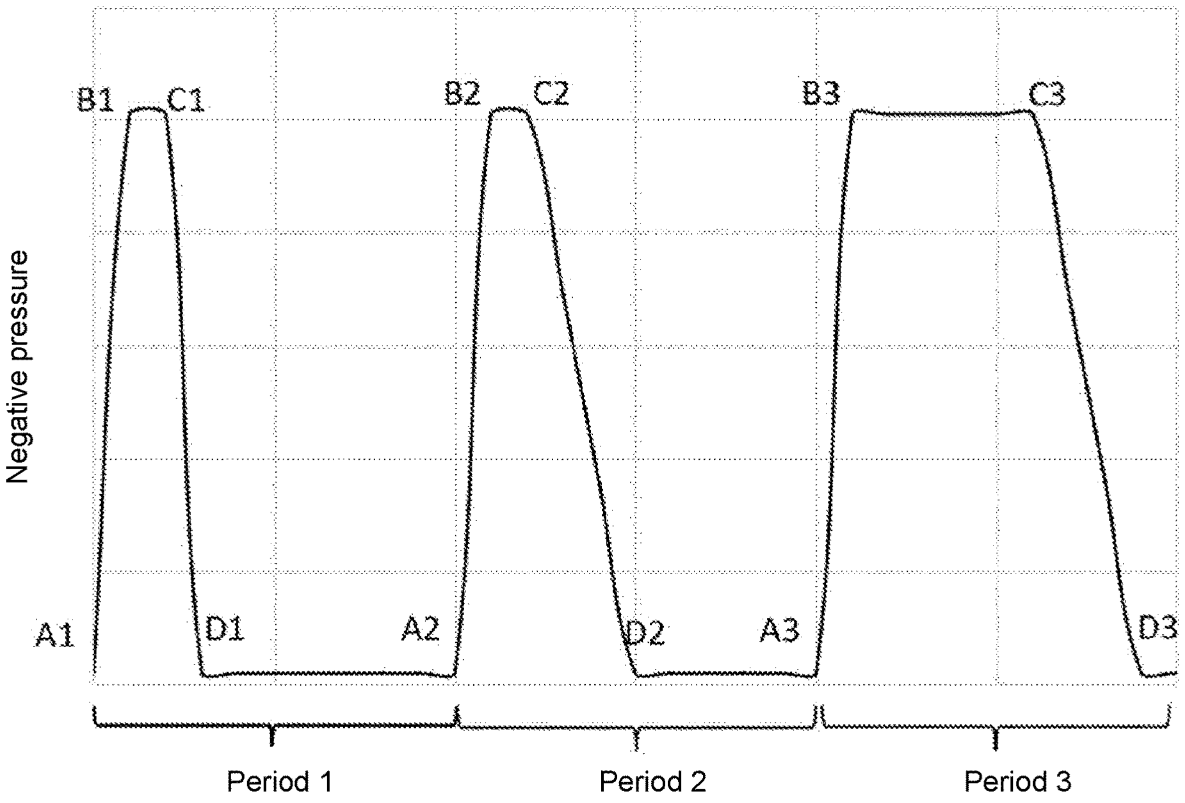
FIG. 8 is a diagram showing suction periods corresponding to different suction states according to one embodiment of the present disclosure.

Further, the control circuit board 3102 determines a target suction state of the suction catheter in accordance with a descending slope of the negative pressure value detected by the pressure sensor 3103 after the electromagnetic valve 3101 is turned off. FIG. 8 shows the change of the negative pressure value detected by the pressure sensor 3103 along with time. As shown in FIG. 8, there are three suction periods. In each period, the electromagnetic valve is turned on at a time point A, so as to perform the suction operation. A maximum negative pressure is generated at a time point B. The electromagnetic valve is turned off at a time point C, and the suction operation is stopped. A minimum negative pressure is generated at a time point D. The control circuit board 3102 controls a start time of the electromagnetic valve 3101 in a next suction period through fitting slope values at the time points C and D. Based on the Poiseuille law, a flow resistance R is constant when the suction catheter and the pipe of the thrombus aspiration connection unit 30 have a same radius. In the blood-drawing state (a volume flow rate is large), a slope value between points C and D is large. In the thrombus-drawing state, the slope value between points C and D decreases gradually along with an increase in a blocking level. In the fully-blocking state, the slope value between points C and D is 0. Hence, it is able to determine the target suction state of the suction catheter 40 in accordance with the descending slope.

After determining the optimum suction strategy through the artificial intelligence algorithm, the thrombus aspiration connection unit 30 further determines whether the current suction state is the blood-drawing state, the thrombus-drawing state or the fully-blocking state in accordance with the descending slope of the negative pressure value detected by the pressure sensor when the air channel is interrupted, and adjust the current suction frequency in accordance with the current suction state, so as to improve the effectiveness and effect of the operation.

The above embodiments are for illustrative purposes only, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. An intelligent thrombus aspiration system, the system comprising:

a negative pressure suction pump, a blood collection tank, a thrombus aspiration connection unit, a suction catheter, and a man-machine interaction module, wherein the thrombus aspiration connection unit is coupled to the negative pressure suction pump and the suction catheter through an air channel, and the blood collection tank is detachably coupled to the thrombus aspiration connection unit, wherein the man-machine interaction module is configured to transmit a target catheter diameter of the suction catheter to the thrombus aspiration connection unit in response to a command for selecting the target catheter diameter, wherein the thrombus aspiration connection unit is configured to:

obtain a plurality of groups of historical treatment data corresponding to the target catheter diameter, each group of historical treatment data at least comprising diagnosis information and suction data;

input target diagnosis information and the plurality of groups of historical treatment data into a neural network, so that a word-to-vector model of the neural network concatenates and vectorizes the diagnosis information in each group of historical treatment data and outputs a plurality of concatenated vectors to a vector fusion model, the vector fusion model being configured to identify the diagnosis information of a same class in each group of historical treatment data;

cluster the historical treatment data corresponding to the suction data having a same class of the diagnosis information and having a deviation value smaller than a predetermined threshold, so as to obtain a plurality of historical treatment data classes;

calculate the quantity of groups of historical treatment data in each historical treatment data class to generate a quantity label, identify class diagnosis information corresponding to each historical treatment data class, and select a matched historical treatment data class in accordance with the target diagnosis information, the quantity label and the class diagnosis information;

take an average value of the suction data in the selected historical treatment data class as target suction data corresponding to the target catheter diameter of the suction catheter; and the thrombus aspiration connection unit further comprises a control circuit board and an electromagnetic valve, the control circuit board is configured to open or close the air channel through controlling the electromagnetic valve to be turned on or off, and the suction frequency is determined in accordance with a switching frequency of the electromagnetic valve.

2. The intelligent thrombus aspiration system according to claim 1, wherein the diagnosis information comprises physiological information, drug information and disease information about a patient.

3. The intelligent thrombus aspiration system according to claim 1, wherein the suction data comprises a suction frequency, a suction duration and a suction negative pressure.

4. The intelligent thrombus aspiration system according to claim 1, wherein the thrombus aspiration connection unit further comprises a pressure sensor in the air channel, and the thrombus aspiration connection unit is further configured to determine a current suction state in accordance with a negative pressure value detected by the pressure sensor after the air channel is closed, and adjust a current suction frequency in accordance with the current suction state.

5. The intelligent thrombus aspiration system according to claim 4, wherein the suction state comprises a blood-drawing state, a thrombus-drawing state, and a fully-blocking state.

6. The intelligent thrombus aspiration system according to claim 1, wherein the thrombus aspiration connection unit further comprises a state indicator and a loudspeaker, and when the current suction state has been determined in accordance with the negative pressure value detected by the pressure sensor, the control circuit board is further configured to control the state indicator to be in an on state and control the loudspeaker to beep.

7. The intelligent thrombus aspiration system according to claim 1, wherein the thrombus aspiration connection unit further comprises a double-row pipe, the double-row pipe comprises an air-channel pipe and a power line pipe, one end of the air-channel pipe is coupled to an internal air channel of the thrombus aspiration connection unit, another end of the air-channel pipe is coupled to the suction catheter through a single-lumen pipe and a Luer taper, one end of the power line pipe is coupled to a switch, and another end of the power line pipe is coupled to the control circuit board.

8. The intelligent thrombus aspiration system according to claim 7, wherein the thrombus aspiration connection unit further comprises the internal air channel and a three-way valve, a first end of the three-way valve is in communication with the internal air channel, a second end of the three-way valve is in communication with the air-channel pipe, and a third end of the three-way valve is coupled to the pressure sensor.

9. The intelligent thrombus aspiration system according to claim 8, wherein the thrombus aspiration connection unit further comprises a sealing joint, one or more protruding sealing rings is arranged in an internal chamber of the sealing joint, one end of the sealing joint is coupled to the internal air channel, another end of the sealing joint is fixed onto a housing of the thrombus aspiration connection unit, the sealing joint is inserted into an opening in a boss of the blood collection tank so that each sealing ring is in hermetical engagement with the boss of the blood collection tank, and an anti-vibration gasket is arranged between the blood collection tank and the housing.

* * * * *